United States Patent [19]

Dillard

[11] Patent Number: 5,105,017

[45] Date of Patent: Apr. 14, 1992

[54] LEUKOTRIENE ANTAGONIST INTERMEDIATES

[75] Inventor: Robert D. Dillard, Zionsville, Ind.

[73] Assignee: Eli Lilly and Company, Indianapolis, Ind.

[21] Appl. No.: 514,428

[22] Filed: Jul. 18, 1983

[51] Int. Cl.⁵ .................. C07C 39/11; C07C 39/06; C07C 149/273

[52] U.S. Cl. ........................ 568/64; 558/9; 568/331; 568/337; 564/365

[58] Field of Search ............... 568/331, 337, 64, 9; 564/365

[56] References Cited

U.S. PATENT DOCUMENTS

| | | | |
|---|---|---|---|
| 3,882,148 | 5/1974 | Augstein et al. | 260/345.2 |
| 3,899,513 | 8/1975 | Warren et al. | 260/345.2 |
| 4,073,935 | 2/1978 | Grill et al. | 424/308 |
| 4,136,192 | 1/1979 | Buckle et al. | 424/281 |
| 4,189,594 | 2/1980 | Vaterstetten et al. | 560/53 |
| 4,281,008 | 7/1981 | Chamberlain et al. | 424/269 |
| 4,474,788 | 10/1984 | Bantick | 424/258 |
| 4,567,201 | 1/1986 | Nohara et al. | 514/571 |

FOREIGN PATENT DOCUMENTS

| | | |
|---|---|---|
| 28063 | 6/1981 | European Pat. Off. . |
| 56172 | 7/1982 | European Pat. Off. . |
| 61800 | 10/1982 | European Pat. Off. . |
| 83228 | 7/1983 | European Pat. Off. . |
| 106565 | 4/1984 | European Pat. Off. . |
| 110541 | 6/1984 | European Pat. Off. . |
| 1555753 | 11/1979 | United Kingdom . |
| 2058785 | 4/1981 | United Kingdom . |

OTHER PUBLICATIONS

Bohlmann et al., "Chem. Berichte", 102, p. 866 (1969).
Chem. Abstr. 99 (1983), Abst. 19461r, Nohava et al., and Berstein et al., Abst. 19462u.
Journal of Medicinal Chemistry, 20(3), 371 (1977).
Journal of Medicinal Chemistry, 22 (2), 158 (1979).
Chem. Ber., 102, 864 (1969).

Primary Examiner—David B. Springer
Attorney, Agent, or Firm—Robert A. Conrad; Leroy Whitaker

[57] ABSTRACT

This invention provides novel benzene derivatives which are leukotriene antagonists, formulations of those derivatives, intermediates for preparing the derivatives, and a method of using those derivatives for the treatment of conditions characterized by an excessive release of leukotrienes.

6 Claims, No Drawings

LEUKOTRIENE ANTAGONIST INTERMEDIATES

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

It is the object of this invention to provide novel chemical agents which are selective leukotriene antagonists that can be used therapeutically in the treatment of allergic disorders such as asthma, where leukotrienes are thought to be causal mediators.

SUMMARY OF THE INVENTION

This invention provides for compounds of the Formula I

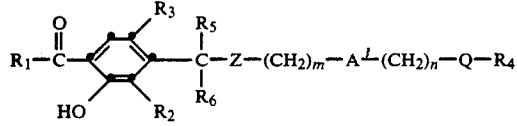

and pharmaceutically acceptable salts thereof, wherein:
$R_1$ is hydrogen, $C_1$-$C_6$ alkyl, $C_3$-$C_8$ cycloalkyl, phenyl-substituted-($C_1$-$C_3$ alkyl), phenyl, or phenyl substituted with halo, $C_1$-$C_4$ alkyl, or $C_1$-$C_4$ alkoxy;
$R_2$ is $C_1$-$C_{10}$ alkyl, $C_2$-$C_6$ alkenyl, benzyl, or 2-phenylethyl;
$R_3$ is hydrogen, bromo, or chloro;
Z is —O—, —NR—, or

or when taken together,

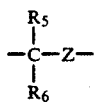

is —CH=CH—;
m is 0–4;
A is a bond, —O—,

—NR'—,

or —CHOH—;
n is 0–4;
Q is a bond, —O—,

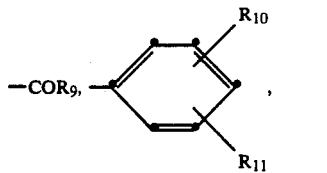

or —NR"—; and
$R_4$ is hydroxy, —SC(=NH)NH$_2$, —NR$_{14}$R$_{15}$,

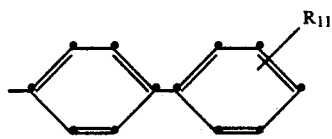

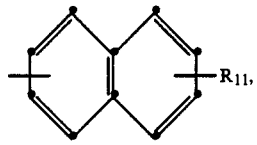

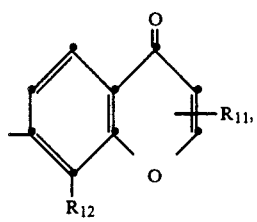

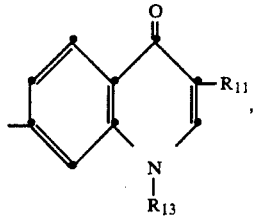

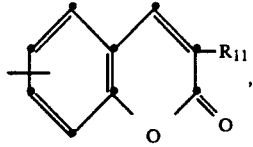

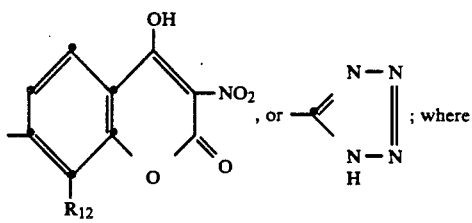

each of R, R', and R" is independently hydrogen or $C_1$-$C_3$ alkyl;
each of $R_5$ and $R_6$ is independently hydrogen, $C_1$-$C_3$ alkyl, phenyl, or benzyl;
$R_9$ is hydroxy, $C_1$-$C_4$ alkoxy, —NHOH, or —NR$_{14}$R$_{15}$;

$R_{10}$ is hydrogen, hydroxy, $C_1$-$C_4$ alkoxy, halo, $C_1$-$C_4$ alkyl, amino, mono- or di-($C_1$-$C_3$ alkyl)amino, or ($C_1$-$C_3$ alkyl)CONH—;

$R_{11}$ is —$(CR_{16}R_{17})_r$—$COR_9$, —O—$(CR_{16}R_{17})_s$—$COR_9$,

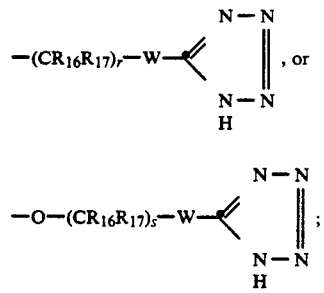

, or $R_{12}$ is hydrogen or $C_1$-$C_3$ alkyl;
$R_{13}$ is hydrogen or methyl;
each of $R_{14}$ and $R_{15}$ is independently hydrogen, $C_1$-$C_3$ alkyl, or when taken together with the nitrogen atom form a morpholine or N-methyl piperazine ring;
each of $R_{16}$ and $R_{17}$ is independently hydrogen or $C_1$-$C_3$ alkyl;
r is 0-4;
s is 1-4;
W is a bond, —O—, —NR'''—, or

R''' is hydrogen or $C_1$-$C_3$ alkyl; and
p is 0, 1, or 2;
provided that:
(a) when $R_4$ is —$COR_9$, hydroxy, —$NR_{11}R_{12}$, or —SC(=NH)$NH_2$, Q may only be a bond and n may not be 0;
(b) when A is —O—,

—NR'—, or —CHOH—, and Z is —O—,

or —NR—, m may not be 0;
(c) when A is —O—,

—NR'—, or —CHOH—, and Q is —O—,

or —NR''—, n may not be 0;
(d) when Z is —O—,

or —NR—, Q is —O—,

or —NR''—, A is a bond, m and n may not both be 0; and
(e) if A is

(1) when Z is

m may not be 0,
(2) when Q is

n may not be 0, and
(3) when Z is —O— or —NR— and Q is —O— or —NR''—, m and n may not both be 0.

Further provided by this invention is a method for treating immediate hypersensitivity conditions such as asthma, using compounds of Formula I above and pharmaceutical formulations for these compounds.

This invention also provides for certain intermediates useful in preparing the compounds of Formula I. These compounds have the general formula

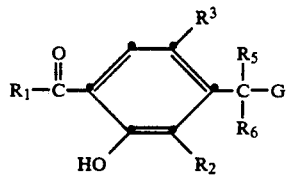

XVI wherein
$R_1$, $R_2$, $R_3$, $R_5$, and $R_6$ are the same as previously defined and G is halo, hydroxy, thiol, —$NR_{18}R_{19}$, or —$P(C_6H_5)_3X'$, where each of $R_{18}$ and $R_{19}$ is independently hydrogen or $C_1$-$C_3$ alkyl, and X' is halo.

This invention also provides for intermediates of the formula

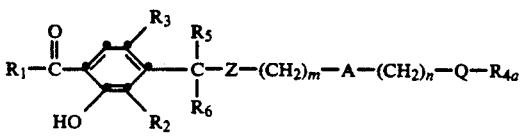

where
$R_1$ is hydrogen, $C_1$-$C_6$ alkyl, $C_3$-$C_8$ cycloalkyl, phenyl-substituted-($C_1$-$C_3$ alkyl), phenyl, or phenyl substituted with halo, $C_1$–$C_4$ alkyl, or $C_1$–$C_4$ alkoxy;

$R_2$ is $C_1$–$C_{10}$ alkyl, $C_2$–$C_6$ alkenyl, benzyl, or 2-phenylethyl;

$R_3$ is hydrogen, bromo, or chloro;

Z is —O—, —NR—, or

or when taken together,

is —CH=CH—;

m is 0–4;

A is a bond, —O—,

—NR'—, —C—, or —CHOH—;

n is 0–4;

Q is a bond, —O—,

or —NR''—; and $R_{4a}$ is —CN,

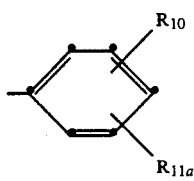

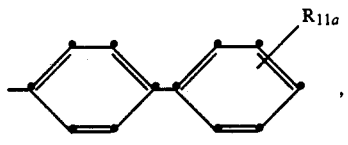

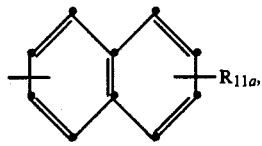

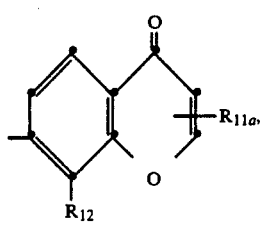

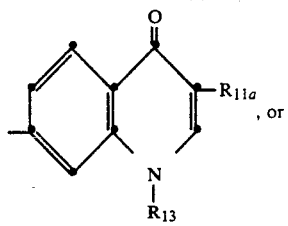

, or

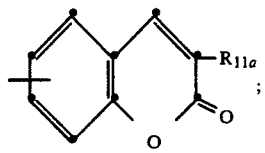

;

where
each of R, R', and R'' is independently hydrogen or $C_1$–$C_3$ alkyl;
each of $R_5$ and $R_6$ is independently hydrogen, $C_1$–$C_3$ alkyl, phenyl, or benzyl;
$R_{10}$ is hydrogen, hydroxy, $C_1$–$C_4$ alkoxy, halo, $C_1$–$C_4$ alkyl, amino, mono- or di-($C_1$–$C_3$ alkyl)amino, or ($C_1$–$C_3$ alkyl)CONH—;
$R_{11a}$ is —$(CR_{16}R_{17})_r$—T—CN or —O—$(CR_{16}R_{17})_s$—T—CN;
$R_{12}$ is hydrogen or $C_1$–$C_3$ alkyl;
$R_{13}$ is hydrogen or methyl;
each of $R_{16}$ and $R_{17}$ is independently hydrogen or $C_1$–$C_3$ alkyl;
r is 0–4;
s is 1–4;
T is a bond or —S—; and
p is 0, 1, or 2;

provided that:
(a) when $R_{4a}$ is —CN, Q may only be a bond or —S—, and n may not be 0;
(b) when A is —O—,

—NR'—, or —CHOH—,
and Z is —O—,

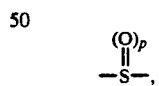

or —NR—, m may not be 0;

(c) when A is —O—,

—NR'—, or —CHOH—, and Q is —O—,

or —NR''—, n may not be 0;

(d) when Z is —O—,

or —NR—, Q is —O—,

or —NR"—, and A is a bond m and n may not both be 0; and (e) if A is $$-\overset{O}{\underset{\|}{C}}-,$$

(1) when Z is

m may not be 0, (2) when Q is

n may not be 0, and (3) when Z is —O— or —NR— and Q is —O— or —NR"—, m and n may not both be 0.

DETAILED DESCRIPTION AND PREFERRED EMBODIMENT

The present invention relates to new organic compounds that are useful in the treatment of immediate hypersensitivity reactions. A preferred group of compounds are the compounds of Formula I wherein:

(a) $R_1$ is $C_1$–$C_6$ alkyl, especially methyl,
(b) $R_2$ is $C_1$–$C_6$ alkyl, especially propyl,
(c) $R_3$ is hydrogen,
(d) $R_5$ is hydrogen,
(e) $R_6$ is hydrogen,
(f) Z is —O—,

or —NH—, and (g) $R_4$ is —COOH, 5-tetrazolyl, or

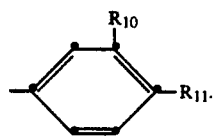

An especially preferred group of compounds are those of Formula Ia:

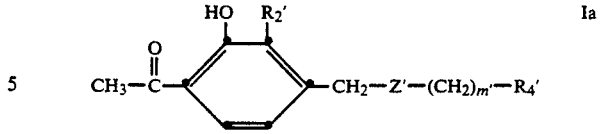

and pharmaceutically acceptable salts thereof wherein:
$R_2'$ is $C_1$–$C_6$ alkyl, especially propyl;
$Z'$ is —O—,

or —NH—;
m' is 2–4; and
$R_4'$ is —COOH, 5-tetrazolyl, or 5-thiotetrazolyl.

A second especially preferred group of compounds are those of Formula Ib:

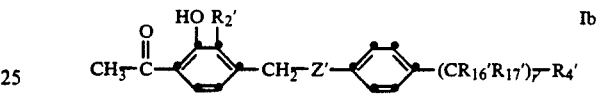

and pharmaceutically acceptable salts thereof wherein:
$R_2'$, $Z'$, and $R_4'$ are the same as described hereinabove;
r' is 0, 1, or 2; and
each of $R_{16}'$ and $R_{17}'$ is independently hydrogen or methyl.

The following definitions refer to the various terms used throughout this disclosure.

The term "$C_1$–$C_{10}$ alkyl" refers to the straight and branched aliphatic radicals of 1 to 10 carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl), nonyl, 1-, 2-, 3-, 4-, 5-, 6-, or 7-methyloctyl, 1-, 2-, 3-, 4-, or 5-ethylheptyl, 1-, 2-, or 3-propylhexyl, decyl, 1-, 2-, 3-, 4-, 5-, 6-, 7-, or 8-methylnonyl, 1-, 2-, 3-, 4-, 5-, or 6-ethyloctyl, 1-, 2-, 3-, or 4-propylheptyl, and the like. The term "$C_1$–$C_{10}$ alkyl" includes within its definition the terms "$C_1$–$C_3$ alkyl", "$C_1$–$C_4$ alkyl", and "$C_1$–$C_6$ alkyl".

The term "$C_3$–$C_8$ cycloalkyl" refers to the saturated alicyclic rings of three to eight carbon atoms such as cyclopropyl, methylcyclopropyl, cyclobutyl, cyclopentyl, cyclohexyl, cyclooctyl, and the like.

The term "$C_2$–$C_6$ alkenyl" refers to straight and branched radicals of two to six carbon atoms such as ethenyl, allyl, isopropenyl, butenyl, isobutenyl, 3-methyl-2-butenyl, n-hexenyl, and the like.

The term "halo" refers to fluoro, chloro, bromo, and iodo. The term "$C_1$–$C_4$ alkoxy" refers to straight and branched alkoxy radicals of up to four carbon atoms, such as methoxy, ethoxy, n-propoxy, isopropoxy, n-butoxy, tert-butoxy, and the like.

The pharmaceutically acceptable base addition salts of this invention include salts derived from inorganic bases, such as ammonium and alkali and alkaline earth metal hydroxides, carbonates, bicarbonates, and the like, as well as salts derived from non-toxic basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

In addition, when the compounds of Formula I are amine derivatives (e.g., $R_4$ is $-NR_{14}R_{15}$ or $-SC(=NH)NH_2$), the compounds may also exist as the corresponding acid addition salts. The pharmaceutically acceptable acid addition salts of this invention therefore also include salts derived from inorganic acids such as hydrochloric acid, nitric acid, phosphoric acid, sulfuric acid, hydrobromic acid, hydriodic acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate, and the like salts. Salts from inorganic acids are preferred, especially the hydrochloride or hydrobromide salts.

It is recognized that if $R_5$ is different from $R_6$, $R_{16}$ is different from $R_{17}$, or if A is $-CHOH$, various stereoisomers will exist. This invention is not limited to any particular stereoisomer but includes all possible individual isomers and racemates of the compounds of Formula I. Similarly, when

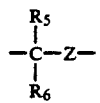

is $-CH=CH-$, both the individual cis and trans isomers and their mixture are included as part of this invention.

Some of the compounds of this invention may be prepared by the reaction of a compound of the Formula II

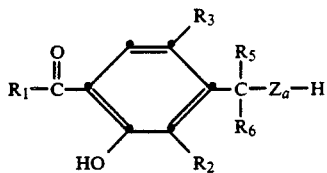

wherein $Z_a$ is $-O-$, $-NR-$, or $-S-$, with a compound of the formula III $$X-(CH_2)_m-A-(CH_2)_n-D \qquad III$$

where X is a suitable leaving group, such as halo, preferably chloro, and D is $-Q-R_4$, a precursor of $-Q-R_4$, halo, cyano, thiocyano, or a protected acid ester such as benzhydryl ester. This procedure is useful in preparing the compounds of this invention designated by formula I'

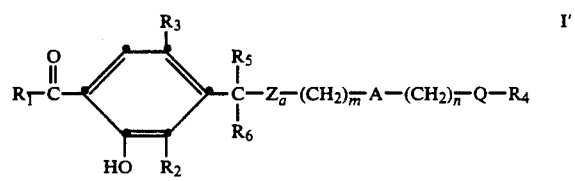

either directly (when D is $-Q-R_4$) or indirectly from intermediates IV

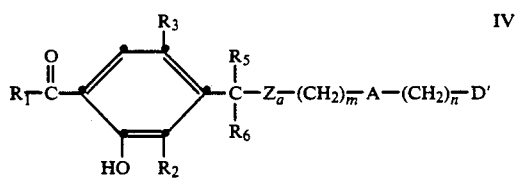

wherein D' is a precursor to $-Q-R_4$, halo, cyano, thiocyano, or a protected acid ester.

The reaction between compounds II and III is usually performed in equimolar amounts although ratios other than equimolar amounts are completely operative. The reaction is best carried out in a nonreactive solvent such as ketones, especially acetone or methyl ethyl ketone, or dimethylformamide, and in the presence of a base, preferably an alkali metal hydroxide or carbonate, preferably potassium carbonate. Especially when X is chloro, a catalyst such as potassium or sodium iodide may be added to increase the reaction rate. The reaction may be carried out at temperatures of about ambient temperature up to the boiling point of the reaction mixture, the latter being preferred.

In the case where D(D') is cyano, the resulting intermediate IV may be converted to the compounds of this invention by the following methods. Compounds of Formula I' wherein $R_4$ is $-COOH$ may be obtained by hydrolysis of the intermediate cyano derivative. This is generally accomplished by heating the cyano derivative in aqueous alcohols in the presence of a base such as sodium hydroxide. Alternatively, the carboxylic acid derivatives (I', $R_4$ is $-COOH$) may be prepared by the hydrolysis of the corresponding ester derivatives. This may be accomplished by an aqueous hydrolysis as described above or, especially in the case of a diphenylmethyl (benzhydryl) ester, using methods known in the art such as treating with formic acid and triethylsilane followed by an aqueous workup, acidic hydrolysis, treatment with trifluoroacetic acid in anisole, or catalytic hydrogenation. The required benzhydryl ester starting materials (III, D is a benzhydryl ester) may be prepared from the corresponding carboxylic acids (III, D is —COOH) in the usual ways, such as treatment with diphenyldiazomethane in methylene chloride or heating with benzhydrol and a mineral acid in a solvent such as toluene with the azeotropic removal of water. The compounds of Formula I' wherein $R_4$ is —COO($C_1$-$C_4$ alkyl) may be prepared by conventional methods of esterification from the respective acid derivatives or are prepared directly by the methods described below. Salts may be prepared by treating the corresponding acids ($R_4$ is —COOH) with an appropriate base in the normal manner. Amide derivatives ($R_4$ is —CONR$_{14}$R$_{15}$ or —CONHOH) may be prepared by direct aminolysis of the corresponding ester, or from the corresponding carboxylic acid using conventional means such as conversion to the acid chloride followed by reaction of the acid chloride with an appropriate amine or treatment with an agent such as 1,1'-carbonyldiimidazole in the presence of an appropriate amine. In either case, the ester or acid is reacted with the appropriate amine V $$HNR_{14}R_{15} \qquad V$$

wherein $R_{14}$ and $R_{15}$ are as described hereinabove, or hydroxylamine, the latter giving the hydroxamic acid derivative.

The above transformations are also applicable in the preparation and intraconversions of the —COR$_9$ derivatives, precursors, and intermediates of $R_{11}$.

The compounds of Formula I' wherein $R_4$ is 5-tetrazolyl (Q is a bond) are prepared by treating the cyano intermediate with an alkali metal azide such as sodium azide, ammonium chloride, and (optionally) lithium chloride in a non-reactive high-boiling solvent such as N,N-dimethylformamide, preferably at temperatures from 60° C. to the reflux temperature of the reaction mixture. Alternatively, tetramethylguanidinium azide may be used in place of the alkali metal azide, ammonium chloride, and lithium chloride. The thiotetrazole compounds of Formula I' (Q is —S—) are prepared from the thiocyano intermediates in a similar manner or may be prepared from a halo intermediate (IV, D' is halo) on treatment with 5-mercaptotetrazole. Certain of the tetrazole functionalities of $R_{11}$ can similarly be prepared from the corresponding nitrile or thiocyano precursors either in the beginning of, in the middle of, or preferably at the end of the other chemical transformations. Thus, it is preferred that the tetrazole functionality be introduced from the corresponding cyano group as one of the last, if not the last step of the chemical sequence.

When employing intermediate III wherein D is halo, those skilled in the art will recognize that when m and n are the same, affording a symmetrically-substituted dihaloalkane III, X and D may be the same or different leaving groups since the reaction with compound II will give the same product IV regardless which "end" of the molecule reacts. However, when alkane III is non-symmetrically substituted, those skilled in the art will recognize that X should be a better leaving group than D in order for the desired product IV to be formed. If D is the better leaving group in compound III, III can first be converted to a different intermediate III (e.g., reaction of III (D is halo) with an alkali metal cyanide to give III (where D is —CN)) which can then be reacted with compound II as previously described.

The compounds of Formula IV wherein D' is halo may be transformed into the compounds of this invention in the following manner. When compounds of Formula IV (D' is halo) are heated with an alkali metal cyanide, such as sodium cyanide, in the presence of a high boiling, nonreactive solvent, such as N,N-dimethylformamide, at elevated temperatures (50° C. to the reflux temperature of the solvent), the intermediate cyano compound of Formula IV (D' is cyano) is produced which may then be transformed into the acid, ester, or tetrazole derivatives as described previously. Simiilarly, the thiotetrazole compounds of this invention can be prepared by reacting a compound of Formula IV (D' is halo) with an alkali metal thiocyanate in a similar manner to give the intermediate thiocyano compound of Formula IV (D' is —SCN) followed by transformation to the thiotetrazole in the usual manner. Alternatively, the thiotetrazole compounds may be prepared from IV (D' is halo) and 5-mercaptotetrazole in a similar manner as previously mentioned.

The compounds of Formula I' wherein $R_4$ is —OH may be prepared directly from the reaction of compound II and a haloalkanol (III, X is halo, D is —OH) or may be prepared from the intermediate IV by aqueous hydrolysis. These compounds may be transformed into other compounds or intermediates of this invention (e.g., where $R_4$ is —CN, etc.) by preparation of the mesylate derivative and displacing with a suitable nucleophile (such as cyanide ion).

The compounds of Formula I' wherein $R_4$ is —NR$_{14}$R$_{15}$ may be prepared by the reaction of the compounds of Formula IV wherein D' is halo with compounds of the Formula V. The reaction of compounds III and V is generally carried out in the presence of a nonreactive, high-boiling solvent such as N,N-dimethylformamide, usually in the presence of a base, preferably an alkali metal carbonate or hydroxide, generally at elevated temperatures up to the boiling point of the solvent.

The isothiourea and thio-, amino-, and oxytetrazole compounds may be prepared from intermediate IV where D' is halo by reacting with thiourea and 5-mercapto-, 5-amino-, and 5-hydroxy-tetrazole, respectively. The reactions are performed by stirring the two reactants in a non-reactive solvent preferably at room to reflux temperature for about two to three days. In the thiourea reaction, ethanol is the preferred solvent and the product is usually isolated as the isothiuronium hydrohalide salt which is formed directly. In the tetrazole reactions, the preferred solvent is dimethylformamide and an acid scavenger, such as an alkali metal carbonate, is preferably included in the reaction.

Alternatively, I' may be prepared by reacting the appropriate benzyl derivative VI

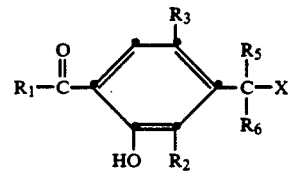

VI with a derivative of Formula VII $H-Z_a-(CH_2)_m-A-(CH_2)_n-D$  VII to give compounds I' directly or indirectly through intermediate IV.

Compounds of Formula I are prepared in a similar manner as taught for the compounds of Formula I'. The compounds of Formula I are prepared directly or indirectly by treating a bromo-compound of the Formula VIII

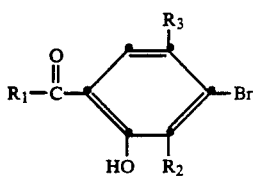
VIII with a strong base, such as lithium diisopropylamide, in an inert solvent, such as diethyl ether, at low temperatures, preferably −20 to 0° C., to prepare the lithium salt of VIII which is then reacted with III'

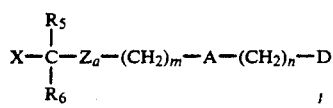
III' to provide compounds I directly (when D is —Q—R$_4$) or intermediates IX.

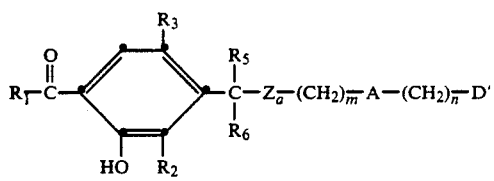
IX

Compounds IX can then be transformed into I by the same methods of transformation as previously described for converting compounds IV into I'.

The alkene derivatives of this invention I''

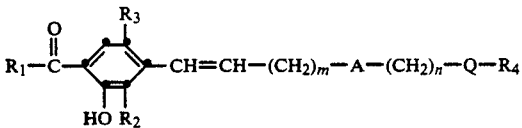
I'' are prepared by reacting a Wittig reagent such as that represented by Formula XI

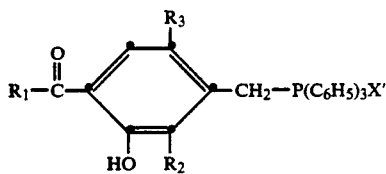
XI with an aldehyde of Formula XII

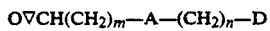

$O\!\!=\!\!CH(CH_2)_m-A-(CH_2)_n-D$  XII to give either compounds I'' directly (D is —Q—R$_4$) or indirectly (D is D') through intermediates XIII. The transformations of intermediate XIII

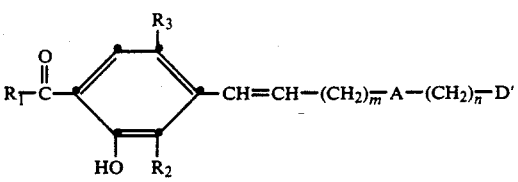
XIII to compounds I'' and the intraconversion of various compounds of Formula I'' are the same as previously described for compounds I and I'. This sequence is limited, as those skilled in the art will appreciate, to those aldehydes XII which may be prepared and are stable to the reaction conditions. For those substituents D which are unstable in the presence of aldehydes and/or Wittig conditions, the desired substituent may be introduced from an intermediate aldehyde after transformation into compound XIII.

Alternatively, the alkene compounds I'' and intermediates XIII can be prepared via the Wittig reaction in the reverse way, i.e., the reaction of benzaldehyde XIV

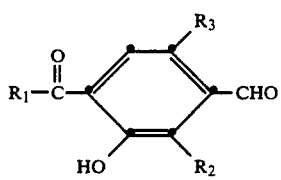
XIV with a Wittig reagent of Formula XV $X'(C_6H_5)_3P-(CH_2)_{m+1}-A-(CH_2)_n-D$  XV subject to the same definitions and limitations as previously described.

The thio derivatives and intermediates of this invention (p is 0) may be transformed into the corresponding sulfoxide (p is 1) compounds upon treatment with a mild oxidizing agent, such as hydrogen peroxide in methanol or an alkali metal periodate in aqueous alcohol. The corresponding sulfones (p is 2) are prepared from the thio or sulfoxide compounds on treatment with a strong oxidizing agent such as hydrogen peroxide in acetic acid or m-chloroperbenzoic acid in methanol.

In addition, various compounds of Formula I can be prepared from other compounds, precursors, or intermediates of Formula I by standard methods such as hydrolysis, esterification, alkylation, oxidation, reduction, aminolysis, halogenation, and the like, as are well known to those skilled in the art. In the prior discussion, the terms "precursors" and "precursor to —Q—R$_4$" mean those compounds, either related to the final compounds I or any intermediates or starting materials, which can be transformed into the desired functionality —Q—R$_4$. These include the cyano intermediates and intermediates which may be transformed into the title products by any of the above mentioned methods known to those skilled in the art. The term also includes alcohol and phenol functionalities which may be alkylated (e.g., a precursor of R$_{11}$ which is —OH that is alkylated with X—(CR$_{17}$R$_{18}$)$_s$—COR$_9$ to give R$_{11}$=—O—(CR$_{17}$R$_{18}$)$_s$—COR$_9$) and other such transformations and intermediates which would be apparent to those skilled in the art.

Intermediate compounds III, V, VI (other than X being halo), VII, VIII, XII, XIII, XIV, and XV are either commercially available, known in the literature, or can be prepared according to methods known in the art.

Intermediates II, VI (X is halo) and XI are novel compounds and are claimed as part of this invention as useful intermediates in the preparation of compounds of Formula I as previously described. More generally, these intermediates are described by the Formula XVI.

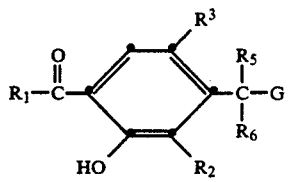

Compounds XVI are generally prepared in the following manner. For example, commercially available 3-methoxybenzyl chloride is treated with a dialkylamine to provide N,N-dialkyl-3-methoxybenzylamine. The $R_2$ functionality can then be introduced by treating the unsubstituted intermediate with a strong base, such as n-butyllithium, in an inert solvent, such as tetrahydrofuran, followed by the addition of the appropriate $R_2$-halide to provide the desired 2-substituted derivative. This alkylation step can be performed a second time in certain cases to provide additional compounds, e.g., the 2-methyl derivative may be treated first with n-butyllithium and then with a 2-halo-propane to provide the 2-isobutyl derivative. The methoxy group is then cleaved by standard methods, such as hydrobromic acid and acetic acid, and the resulting phenol is then acylated with the appropriate $R_1$-acid halide or anhydride in the usual way. Heating the 3-acyloxy compound in the presence of aluminum chloride or other Lewis acid catalysts (the Fries rearrangement) provides the desired N,N-dialkylbenzylamine compounds of Formula XVI ($R_{18}$ and $R_{19}$ are each independently $C_1-C_3$ alkyl). These intermediates can then be transformed into the desired benzyl halide intermediates (XVI, G is halo) on treatment with an alkyl haloformate, such as ethyl chloroformate. These benzyl halide intermediates are useful both as intermediates to the compounds of Formula I by the reaction involving compounds VI (X is halo) and are also useful in preparing the other intermediates of this invention.

For example, the other amine intermediates of this invention (II, $Z_a$ is —NR—, or XVI, G is —$NR_{18}R_{19}$ where one of $R_{18}$ and $R_{19}$ is hydrogen and the other of $R_{18}$ and $R_{19}$ is hydrogen or $C_1-C_3$ alkyl) are prepared by reacting the corresponding benzyl halide with ammonia or the appropriate alkylamine by standard methods known in the art. Likewise, the benzyl halide can be transformed into the benzyl alcohol (II, $Z_a$ is —O—, or XVI, G is hydroxy) by standard means of basic hydrolysis. The benzyl mercaptan intermediates are prepared from the corresponding benzyl halide compounds by first treating with thiourea to provide an intermediate isothiuronium halide derivative which is transformed into the desired mercaptan intermediates (II, $Z_a$ is —S—, or XVI, G is thiol) by standard methods of basic hydrolysis. The Wittig intermediates (XI, or XVI, G is —$P(C_6H_5)_3X'$) are prepared by known methods which usually simply employ the heating of the corresponding benzyl halide with triphenylphosphine in an inert solvent such as toluene.

As will be appreciated by those skilled in the art, the preparation of intermediates XVI where $R_5$ and $R_6$ are other than hydrogen may also be prepared in the same manner as previously described. An alternate method of preparation involves the addition of the $R_5$ or $R_6$ groups (other than hydrogen) to the corresponding α-unsubstituted benzyl intermediate after the $R_2$-functionality has been introduced. For example, the N,N-dialkyl-3-methoxy-2-($R_2$)-benzyl amine compounds as described above may be transformed into a corresponding benzyl halide in the usual manner which is then converted to the benzaldehyde by any of a number of transformations known in the art, especially treatment with sodium and 2-nitropropane. See, e.g., J. Am. Chem. Soc., 71, 1769 (1949). The benzaldehyde is then treated with the appropriate Grignard reagent to give the corresponding α-substituted benzyl alcohol. If an α,α-disubstituted derivative is desired, the α-substituted benzyl alcohol can be oxidized to the corresponding ketone and treated once again with a Grignard reagent. The α-mono- or α,α-di-substituted benzyl alcohol can then be converted into the corresponding benzyl halide (e.g., treatment with thionyl chloride and pyridine to give the benzyl chloride) which is then added to a dialkylamine to give the desired N,N-dialkylbenzylamine which can then be demethylated, acylated, rearranged, etc. as previously described.

As is well known in the art, the $R_3$ chloro and bromo derivatives may be prepared by halogenation of the corresponding hydrogen compounds ($R_3$ is hydrogen) of this invention (I) or of the intermediates XVI.

The following preparations and examples further illustrate the preparation of the starting materials, intermediates, and compounds of this invention. The examples are illustrative only and are not intended to limit the scope of the invention. Where structures were confirmed by infra-red or proton nuclear magnetic resonance analysis, the compound is so designated by "IR" and/or "NMR", respectively.

PREPARATION 1

N,N-dimethyl-3-methoxybenzylamine

Four hundred grams of dimethylamine were added to 1.5 liters of acetonitrile previously cooled with an external ice/ethanol bath. To this solution were added 322.7 g. of 3-methoxybenzyl chloride in a dropwise fashion. When the addition was completed, the reaction was stirred for an additional four hours with cooling. The reaction was stirred an additional 20 hours at room temperature, heated to reflux for five hours, and then concentrated under reduced pressure. The residue was taken up in water, the aqueous solution was made strongly basic with aqueous sodium hydroxide, and the solution was then extracted with diethyl ether. The ether layer was first washed with water and then extracted with dilute hydrochloric acid. The acid layer was made basic with an aqueous sodium hydroxide solution and extracted with diethyl ether. The layer was dried over sodium sulfate and evaporated to dryness. The residue was vacuum distilled at 3 torr. The fraction between 88 and 92° C. afforded 257 g. of the desired title intermediate. NMR.

PREPARATION 2

N,N-dimethyl-3-methoxy-2-propylbenzylamine

Under an argon atmosphere, 420 ml. of a 1.6M solution of n-butyllithium in hexane were slowly added to a solution of 105.6 g. of N,N-dimethyl-3-methoxybenzylamine in 1000 ml. of tetrahydrofuran by means of an addition funnel, keeping the temperature below 0° C. with an external ice/ethanol bath. After the addition was completed, the reaction was stirred at 0° C. for four hours. At this time, 68.3 ml. of 1-iodopropane were added dropwise to the solution keeping the temperature below 10° C. The reaction was stirred for one hour. The cooling bath was removed and the reaction was stirred an additional two hours. The reaction was then heated to reflux for about 16 hours. The reaction solution was concentrated in vacuo and the residue was taken up in diethyl ether. The ether solution was first washed with an aqueous sodium hydroxide solution and then with water. The ether layer was dried over sodium sulfate and the solvent was removed in vacuo. The residue was vacuum distilled at 3 torr. The fraction collected between 105 and 115° C. provided 104.3 g. of the desired title intermediate. NMR, IR.

The following intermediates were prepared in the same manner using the appropriate alkyl iodide:

N,N-dimethyl-3-methoxy-2-ethylbenzylamine, b.p. 105°–110° C./3 torr, NMR, IR.

N,N-dimethyl-3-methoxy-2-methylbenzylamine, b.p. 47° C./0.08 torr, NMR, IR.

Following the same procedure, N,N-dimethyl-3-methoxy-2-methylbenzylamine (28.64 g.) was treated with butyllithium and 2-iodopropane to provide 7.2 g. of N,N-dimethyl-3-methoxy-2-(2-methylpropyl)benzylamine,
b.p. 118°–126° C./3 torr, IR, NMR.

PREPARATION 3

N,N-dimethyl-3-methoxy-2-propyl-α-methylbenzylamine

Fifty-seven milliliters of ethyl chloroformate were added dropwise to a solution of 41.4 g. of N,N-dimethyl-3-methoxy-2-propylbenzylamine in 500 ml. of benzene with external ice bath cooling. The reaction was stirred at room temperature for 20 hours at which time 100 ml. of water were added. The mixture was stirred an additional hour and the layers were then separated. The benzene layer was washed with water, dried over sodium sulfate, and evaporated to dryness. The residue was vacuum distilled. The fraction at 112°–120° C./3 torr provided 36.5 g. of the desired 3-methoxy-2-propylbenzyl chloride intermediate.

Ten grams of this benzyl chloride intermediate were added to a solution of 1.15 g. of sodium metal in 50 ml. of ethanol in which 5.8 g. of 2-nitropropane had also been added. The reaction was heated to reflux for 2.5 hours and then allowed to cool. The mixture was filtered and the solvent was removed from the filtrate by evaporation in vacuo. The residue was dissolved in diethyl ether and the solution was washed sequentially with water, twice with a 10% aqueous sodium hydroxide solution, and a saturated sodium chloride solution. The organic solution was dried over sodium sulfate and evaporated to dryness. The residue was vacuum distilled. The fraction at 128°–133° C./3 torr provided 7.4 g. of 3-methoxy-2-propylbenzaldehyde.

To a solution of 84.8 g. of 3-methoxy-2-propylbenzaldehyde in one liter of diethyl ether were added 349.6 ml. of a 2.86 M solution of methyl magnesium bromide in diethyl ether with the reaction mixture cooled by means of an external ice/ethanol bath. The reaction was stirred for three hours with cooling and 48 hours at room temperature. The reaction was allowed to stand an additional 24 hours at which time 120 ml. of a saturated ammonium chloride solution were slowly added. The ether was removed from the resulting solid and the solid was triturated twice with ether. The combined ether layers were dried over magnesium sulfate and the solvent was removed by evaporation. The residue was distilled. The fraction at 83°–90° C. and 0.1 torr provided 82.2 g. of 3-methoxy-2-propyl-α-methylbenzyl alcohol.

To a solution of 82 g. of 3-methoxy-2-propyl-α-methylbenzyl alcohol, 33.7 ml. of pyridine, and 1 ml. of water in one liter of methylene chloride were added 43.5 ml. of thionyl chloride with the reaction mixture cooled by means of external ice/water bath. The reaction mixture was stirred 1.5 hours with cooling at which time 100 ml. of water were added. The mixture was stirred an additional 30 minutes and more water was added. The layers were separated and the organic layer was washed with a sodium bicarbonate solution and then with water. The organic solution was dried over sodium sulfate and the solution was evaporated in vacuo. The residual oil was added dropwise to a solution of 150 g. of anhydrous dimethylamine in one liter of acetonitrile which was cooled with an external ice/ethanol bath. The solution was stirred for two hours with cooling and 48 hours at room temperature. The reaction mixture was concentrated under reduced pressure and the residue was dissolved in ether. The solution was first washed with a sodium hydroxide solution and then with water. The organic solution was then extracted with three liters of a dilute hydrochloric acid solution. The acid extract was made basic with sodium hydroxide and the aqueous solution was extracted with ether. The ether extract was dried over sodium sulfate and evaporated to dryness. Vacuum distillation of the residue at 80°–85° C./0.2 torr yielded 66.6 g. of N,N-dimethyl-3-methoxy-2-propyl-α-methylbenzylamine. IR, NMR.

Analysis: $C_{14}H_{23}NO$;

Calc.: C, 75.96; H, 10.47; N, 6.33;

Found: C, 75.72; H, 10.23; N, 6.29.

PREPARATION 4

N,N-dimethyl-3-hydroxy-2-methylbenzylamine hydrobromide

A solution of 37.6 g. of N,N-dimethyl-3-methoxy-2-methylbenzylamine in 150 ml. of 48% hydrobromic acid and 350 ml. of acetic acid was heated to reflux for 72 hours. The reaction mixture was concentrated under reduced pressure. Ethanol (500 ml.) was added to the residue and the solution was evaporated in vacuo. The residue was crystallized from ethanol/isopropyl ether to provide 31.9 g. of the title intermediate, m.p. 215°–217° C., NMR, IR.

Following the same procedure, the following compounds were prepared from the appropriate methoxy precursors:

N,N-dimethyl-3-hydroxy-2-ethylbenzylamine hydrobromide, m.p. 200°–202° C., NMR, IR.

N,N-dimethyl-3-hydroxy-2-propylbenzylamine hydrobromide, m.p. 154°–155° C., NMR, IR.

N,N-dimethyl-3-hydroxy-2-(2-methylpropyl)-benzylamine hydrobromide, m.p. 150°-152° C., NMR, IR.

N,N-dimethyl-3-hydroxy-2-propyl-α-methylbenzylamine, b.p. 100°-105° C./0.05 torr, NMR, IR.

PREPARATION 5

N,N-dimethyl-3-acetoxy-2-propylbenzylamine hydrochloride

To a solution of 83 g. of N,N-dimethyl-3-hydroxy-2-propylbenzylamine hydrobromide in 40 ml. of pyridine, 3 g. of 4-(dimethylamino)pyridine, and one liter of methylene chloride cooled by means of an external ice bath were added 32.3 ml. of acetyl chloride. After stirring two hours with cooling, 150 ml. of water were added and a solution was stirred an additional 30 minutes. The reaction was then treated with a large excess of a potassium carbonate solution and the layers were separated. The methylene chloride layer was washed with water, dried over sodium sulfate, and was evaporated in vacuo. The residue was distilled at 64°-77° C./0.01-0.04 torr to provide 65 g. of the free base of title product. The distillate was dissolved in 800 ml. of acetone, cooled, and treated with dry hydrogen chloride gas. After the solution was saturated, gas addition was stopped and one liter of diethyl ether was added. After standing overnight, the solution was filtered to provide 70.1 g. of the title product hydrochloride salt, m.p. 168°-173° C., NMR, IR.

Following the same procedure, the following compounds were prepared from the respective phenol intermediate and the appropriate acyl chloride:

N,N-dimethyl-3-acetoxy-2-methylbenzylamine hydrochloride, m.p. 203°-205° C., NMR, IR.

N,N-dimethyl-3-acetoxy-2-ethylbenzylamine hydrochloride, m.p. 170°-172° C., NMR, IR.

N,N-dimethyl-3-pentanoyloxy-2-propylbenzylamine hydrochloride, m.p. 146°-148° C., NMR, IR.

N,N-dimethyl-3-benzoyloxy-2-propylbenzylamine hydrobromide, m.p. 150°-152° C., NMR, IR.

N,N-dimethyl-3-acetoxy-2-(2-methylpropyl)benzylamine hydrochloride, m.p. 205°-208° C., NMR, IR.

N,N-dimethyl-3-acetoxy-2-propyl-α-methylbenzylamine hydrochloride, m.p. 188°-190° C., NMR, IR.

PREPARATION 6

N,N-dimethyl-4-acetyl-3-hydroxy-2-propylbenzylamine

Dry N,N-dimethyl-3-acetoxy-2-propylbenzylamine hydrochloride (27.2 g.) was heated in a flask to 162°-166° C. by means of an external oil bath. After about 15 minutes, 26.7 g. of aluminum chloride were added and the heating continued at 165°-166° C. for two hours. The reaction was allowed to cool. To the residue were added 500 ml. of methylene chloride, 300 ml. of water, and 150 g. of potassium carbonate. After the residue had dissolved, additional water and methylene chloride were added. The organic layer was separated, dried over sodium sulfate, and the solvent was removed by evaporation. The residue was distilled at 99°-102° C./−0.2 torr to provide 9.7 g. of the desired title intermediate, NMR, IR.

Analysis: $C_{14}H_{21}NO_2$;

Calc. C, 71.46; H, 9.00; N, 5.95.

Found: C, 71.16; H, 8.77; N, 6.08.

Following the same procedure, the following compounds were prepared from the corresponding 3-acyloxy intermediates:

N,N-dimethyl-4-acetyl-3-hydroxy-2-methylbenzylamine, b.p. 94°-98° C./0.2 torr, NMR, IR.

Analysis $C_{12}H_{17}NO_2$;

Calc.: C, 69.54; H, 8.27; N, 6.76.

Found: C, 69.55; H, 7.99; N, 7.08.

N,N-dimethyl-4-acetyl-3-hydroxy-2-ethylbenzylamine, b.p. 90°-92° C./0.2 torr, NMR, IR.

Analysis: $C_{13}H_{19}NO_2$;

Calc. C, 70.56; H, 8.65; N, 6.33.

Found: C, 70.85; H, 8.75; N, 6.58.

N,N-dimethyl-4-acetyl-3-hydroxy-2-(2-methylpropyl)benzylamine, b.p. 105°-110° C./0.1 torr, NMR, IR.

Analysis: $C_{15}H_{23}NO_2$;

Calc.: C, 72.25; H, 9.30; N, 5.62;

Found: C, 72.06; H, 9.13; N, 5.60.

N,N-dimethyl-4-acetyl-3-hydroxy-2-propyl-α-methylbenzylamine, b.p. 100°-103° C./0.2 torr.

Analysis: $C_{15}H_{23}NO_2$;

Calc.: C, 72.25; H, 9.30; N, 5.62.

Found: C, 72.08; H, 9.10; N, 5.40.

N,N-dimethyl-4-pentanoyl-3-hydroxy-2-propylbenzylamine, b.p. 110°-125° C./0.1 torr, NMR, IR.

N,N-dimethyl-4-benzoyl-3-hydroxy-2-propylbenzylamine, NMR, IR.

PREPARATION 7

4-Acetyl-3-hydroxy-2-propylbenzyl chloride

To a solution of 98.3 g. of N,N-dimethyl-4-acetyl-3-hydroxy-2-propylbenzylamine in 200 ml. of benzene and 500 ml. of toluene cooled by means of an external ice-water bath were added 120 ml. of ethyl chloroformate in a dropwise fashion. After the addition was completed, the reaction was stirred for two hours. The cooling bath was removed and the reaction was stirred for 20 hours at room temperature. Two hundred milliliters of water were then added to the reaction and the solution was stirred for two hours. More water was added to the solution and the layers were separated. The benzene layer was washed with water, dried over sodium sulfate, and the solvent was removed in vacuo. The residue was distilled and the fraction collected at 105°-125° C. and 0.2 torr was further purified by high pressure liquid chromatography over silica gel The appropriate fractions were pooled and evaporated affording 65.0 g. of the title intermediate, NMR, IR.

Analysis: $C_{12}H_{15}ClO_2$;

Calc.: C, 63.58; H, 6.67.

Found: C, 63.46; H, 6.64

Employing the same procedure, the following benzyl chloride intermediates were prepared from the corresponding dimethylbenzylamine derivatives:

4-Acetyl-3-hydroxy-2-methylbenzyl chloride, b.p. 190°-200° C./3 torr, NMR, IR.

4-Acetyl-3-hydroxy-2-ethylbenzyl chloride, b.p. 120°-130° C./0.5 torr, NMR, IR.

Analysis: $C_{11}H_{13}ClO_2$;

Calc. C, 62.12; H, 6.16;

Found: C, 62.07; H, 5.88.

4-Pentanoyl-3-hydroxy-2-propylbenzyl chloride, NMR, IR.

4-Benzoyl-3-hydroxy-2-propylbenzyl chloride, NMR, IR.

4-Acetyl-3-hydroxy-2-(2-methylpropyl)benzyl chloride, NMR, IR.

Analysis: $C_{13}H_{17}ClO_2$;

Calc.: C, 64.86; H, 7.12.

Found: C, 65.11; H, 6.99.

PREPARATION 8

4-Acetyl-3-hydroxy-2-propylbenzyl alcohol

A solution of 4.52 g. of 4-acetyl-3-hydroxy-2-propylbenzyl chloride and 8.2 g. of sodium acetate in 75 ml. of acetic acid were heated to reflux for five days. The acetic acid was removed by evaporation and the residue was taken up in ethyl acetate. The organic solution was washed successively with water, an aqueous sodium bicarbonate solution, and water again. The solution was dried over sodium sulfate and evaporated in vacuo to provide 5.0 g. of the acetate ester of the title alcohol.

The ester was heated to reflux for six days in 50 ml. of methanol and 0.41 ml. of triethylamine. After stirring an additional three days at room temperature, the reaction mixture was poured into water and extracted with ethyl acetate. The organic solution was dried over sodium sulfate and evaporated to dryness. The residue was vacuum distilled at 113°-122° C./−0.07 torr to give 3.2 g. of the title alcohol, m.p. 60°-62° C., NMR, IR.

Analysis $C_{12}H_{16}O_3$;
Calc C, 69.21; H, 7.74.
Found C, 68.92; H, 7.57.

PREPARATION 9

4-Acetyl-3-hydroxy-2-propylbenzyl mercaptan

A solution of 22.7 g. of 4-acetyl-3-hydroxy-2-propylbenzyl chloride and 9.5 g. of thiourea in 350 ml. of ethanol was heated to reflux for 24 hours. The reaction mixture was evaporated to dryness in vacuo and the residue was crystallized from ethanol/diethyl ether to provide 23.4 g. of the desired isothiuronium chloride intermediate, m.p. 193°-195° C., IR, NMR.

Under an argon atmosphere, a mixture of 23.3 g. of the isothiuronium chloride intermediate prepared above, 66.8 ml. of 5N sodium hydroxide and 200 ml. of water was heated to reflux for three hours. The mixture was cooled by means of an external ice bath, made acidic with hydrochloric acid, and was extracted with methylene chloride. The organic extract was dried over sodium sulfate and evaporated to dryness providing 16.8 g. of the desired mercaptan intermediate. NMR, IR.

Analysis: $C_{12}H_{16}O_2S$;
Calc.: C, 64.25; H, 7.19.
Found: C, 64.44; H, 7.44.

EXAMPLE 1

7-(4-Acetyl-3-hydroxy-2-propylbenzyloxy)-4-oxo-8-propyl-4H-1-benzopyran-2-carboxylic acid, ethyl ester To a suspension of 5.8 g. of a 50% sodium hydride suspension in oil, previously washed with toluene in 250 ml. of dimethylformamide were added 24.8 g. of 7-hydroxy-4-oxo-8-propyl-4H-1-benzopyran-2-carboxylic acid ethyl ester in portions. After stirring for one hour, 6.8 g. of 4-acetyl-3-hydroxy-2-propylbenzyl chloride were added and the reaction was stirred for 48 hours. The reaction was then diluted with one liter of water and made acidic with concentrated hydrochloric acid. The solution was extracted with two liters of ethyl acetate. The ethyl acetate extract was washed twice with water and dried over sodium sulfate. The solvent was removed by evaporation and the resulting residue was heated with 300 ml. of ethyl acetate. The slurry was filtered hot and the filtrate was allowed to cool. On cooling a precipitate formed which was removed by filtration. The filtrate was evaporated to dryness and the residue was purified by chromatography over silica gel eluting with 4:1 toluene/ethyl acetate. The desired fractions were collected, combined, and evaporated to dryness to provide 0.6 g. of the desired title product.

Analysis: $C_{27}H_{30}O_7$;
Calc.: C, 69.51; H, 6.48.
Found: C, 69.38; H, 6.40.

EXAMPLES 2-9

Following the general procedure of Example 1, the following compounds were prepared from the appropriate benzyl chloride and phenol derivatives. All compounds were characterized by their IR, NMR, and mass spectra.

2. Ethyl 4-(4-acetyl-3-hydroxy-2-propylbenzyloxy)benzoate.
3. Ethyl 4-(4-acetyl-3-hydroxy-2-propylbenzyloxy)phenylacetate.
4. Ethyl 4-(4-acetyl-3-hydroxy-2-propyl-benzyloxy)-2-hydroxybenzoate.
5. Ethyl 3-(4-acetyl-3-hydroxy-2-propylbenzyloxy)phenylbenzoate.
6. Ethyl 3-[4-(4-acetyl-3-hydroxy-2-propylbenzyloxy)phenyl]propionate.
7. Ethyl 4-(4-acetyl-3-hydroxy-2-propylbenzyloxy)phenoxyacetate.
8. Ethyl 4-(4-benzoyl-3-hydroxy-2-propylbenzyloxy)benzoate.

Analysis $C_{26}H_{26}O_5$;
Calc.: C, 74.62; H, 6.26.
Found: C, 74.86; H, 6.46.

9. Ethyl 4-(4-pentanoyl-3-hydroxy-2-propylbenzyloxy)phenylacetate.

EXAMPLE 10

7-(4-Acetyl-3-hydroxy-2-propylbenzyloxy)-4-oxo-8-propyl-4H-1-benzopyran-2-carboxylic acid A solution of 0.6 g. of the ethyl ester from Example 1 and 4.5 g. of sodium bicarbonate was heated to reflux in 100 ml. of ethanol and 25 ml. of water for four hours. The solution was then concentrated under reduced pressure. The residue was taken up in water. The solution was made acidic with hydrochloric acid and extracted with ethyl acetate. The ethyl acetate was washed with water, dried over sodium sulfate, and evaporated to dryness. The residue was crystallized from ethanol/water to afford 0.2 g. of the desired title product, m.p. 195°-205° C.

Analysis: $C_{25}H_{28}O_7$;
Calc C, 68.17; H, 6.41.
Found: C, 68.23; H, 6.21.

EXAMPLES 11-18

Following the general procedure of Example 10, the following acid derivatives were prepared from the corresponding esters of Examples 2-9:

11. 4-(4-Acetyl-3-hydroxy-2-propylbenzyloxy)benzoic acid, m.p. 192°-194° C.

Analysis: $C_{19}H_{20}O_5$;
Calc.: C, 69.50; H, 6.14.
Found: C, 69.61; H, 6.27.

12. 4-(4-Acetyl-3-hydroxy-2-propylbenzyloxy)phenylacetic acid, m.p. 140°-142° C.

Analysis: $C_{20}H_{22}O_5$;
Calc. C, 70.16; H, 6.48.
Found: C, 70.42; H, 6.57.

13. 4-(4-Acetyl-3-hydroxy-2-propylbenzyloxy)-2-hydroxybenzoic acid, m.p. 176°–178° C.
Analysis: $C_{19}H_{20}O_6$;
Calc.: C, 66.27; H, 5.85.
Found: C, 66.06; H, 5.65.

14. 3-(4-Acetyl-3-hydroxy-2-propylbenzyloxy)benzoic acid, m.p. 182°–184° C.
Analysis: $C_{19}H_{20}O_5$;
Calc.: C, 69.50; H, 6.14.
Found: C, 69.76; H, 5.94.;

15. 3-[4-(4-Acetyl-3-hydroxy-2-propylbenzyloxy)phenyl]propionic acid, m.p. 126°–128° C.
Analysis: $C_{21}H_{24}O_5$;
Calc C, 70.77; H, 6.79.
Found: C, 71.00; H, 6.88.

16. 4-(4-Acetyl-3-hydroxy-2-propylbenzyloxy)phenoxyacetic acid, m.p. 92°–94° C.
Analysis $C_{20}H_{22}O_6$;
Calc.: C, 67.03; H, 6.19.
Found: C, 67.01; H, 5.94.

17. 4-(4-Benzoyl-3-hydroxy-2-propylbenzyloxy)benzoic acid, m.p. 168°–170° C.
Analysis: $C_{24}H_{22}O_5$;
Calc.: C, 73.83; H, 5.68;
Found: C, 73.89; H, 5.95.

18. 4-(4-Pentanoyl-3-hydroxy-2-propylbenzyloxy)phenylacetic acid, IR, NMR.

EXAMPLE 19

4-(4-Acetyl-3-hydroxy-2-propylbenzyloxy)benzonitrile

The title nitrile intermediate was prepared from 18.12 g. of 4-acetyl-3-hydroxy-2-propylbenzyl chloride and 35.7 g. of 4-cyanophenol following the general procedure of Example 1. Crystallization from ethanol/water provided 19.0 g. of the desired intermediate, m.p. 102°–103° C.
Analysis: $C_{19}H_{19}NO_3$;
Calc.: C, 73.77; H, 6.19; N, 4.53.
Found: C, 73.59; H, 6.06; N, 4.28.

EXAMPLES 20–31

Following the general procedure of Example 19, the following nitrile intermediates were prepared from the appropriate benzyl derivative and the corresponding nitrile intermediate:

20. 4-(4-Acetyl-3-hydroxy-2-propylbenzyloxy)phenylacetonitrile, m.p. 102°–104° C.
Analysis: $C_{20}H_{21}NO_3$;
Calc.: C, 74.28; H, 6.55; N, 4.33.
Found: C, 74.52; H, 6.72; N, 4.30.

21. 4-(4-Acetyl-3-hydroxy-2-propylbenzyloxy)-2-hydroxybenzonitrile, NMR, IR.
Analysis: $C_{19}H_{19}NO_4$;
Calc C, 70.14; H, 5.89; N, 4.31.
Found C, 70.18; H, 5.90; N, 4.24.

22. 3-[4-(4-Acetyl-3-hydroxy-2-propylbenzyloxy)phenyl propionitrile, m.p. 63°–64.5° C.
Analysis: $C_{21}H_{23}NO_3$;
Calc.: C, 74.75; H, 6.87; N, 4.15.
Found: C, 75.09; H, 6.88; N, 4.05.

23. 2-[4-(4-Acetyl-3-hydroxy-2-propylbenzyloxy)phenyl]propionitrile, m.p. 73°–74° C.
Analysis: $C_{21}H_{23}NO_3$;
Calc.: C, 74.75; H, 6.87; N, 4.15;
Found: C, 74.97; H, 7.03; N, 3.93.

24. 2-Methyl-2-[4-(4-acetyl-3-hydroxy-2-propylbenzyloxy)phenyl]propionitrile, NMR.

25. 4-(4-Acetyl-3-hydroxy-2-propylbenzylthiomethyl)benzonitrile, NMR, IR.
Analysis: $C_{20}H_{21}NO_2S$;
Calc.: C, 70.77; H, 6.24; N, 4.13.
Found: C, 70.49; H, 6.20; N, 3.97.

26. 4-(4-Acetyl-3-hydroxy-2-methylbenzyloxy)benzonitrile, NMR.

27. 4-(4-Acetyl-3-hydroxy-2-propylbenzylthio)benzonitrile, m.p. 109°–110° C., IR, NMR.
Analysis: $C_{19}H_{19}NO_2S$;
Calc.: C, 70.13; H, 5.89; N, 4.30.
Found: C, 70.31; H, 6.16; N, 4.59.

28. 6-(4-Acetyl-3-hydroxy-2-propylbenzyloxy)-2-naphthonitrile.
Analysis: $C_{23}H_{21}NO_3$;
Calc C, 76.86; H, 5.89; N, 3.90.
Found C, 76.64; H, 6.01; N, 3.97.

29. 4-[4-Acetyl-3-hydroxy-2-(2-methylpropyl)benzyloxy]phenylacetonitrile.
Analysis: $C_{21}H_{23}NO_3$;
Calc.: C, 74.75; H, 6.87; N, 4.15.
Found: C, 74.45; H, 6.93; N, 3.94.

30. 4-(4-Acetyl-3-hydroxy-2-propylbenzylamino)phenylacetonitrile, m.p. 74°–76° C.
Analysis: $C_{20}H_{22}N_2O_2$;
Calc. C, 74.51; H, 6.88; N, 8.69.
Found: C, 74.49; H, 6.77; N, 8.91.

31. 4-(4-Acetyl-3-hydroxy-2-ethylbenzyloxy)phenylacetonitrile, m.p. 100°–102° C.
Analysis: $C_{19}H_{19}NO_3$;
Calc.: C, 73.77; H, 6.19; N, 4.53.
Found: C, 74.05; H, 6.28; N, 4.44.

EXAMPLE 32

5-[4-(4-Acetyl-3-hydroxy-2-propylbenzyloxy)phenyl]-tetrazole

A solution of 19.0 g. of 4-(4-acetyl-3-hydroxy-2-propylbenzyloxy)benzonitrile, 13.0 g. of sodium azide, and 10.9 g. of ammonium chloride in 250 ml. of dimethylformamide was heated to 115° C. for eight hours. An additional 13.0 g. of sodium azide and 10.9 g. of ammonium chloride were added every 2.5 hours during this period. The reaction was stirred overnight at room temperature and then heated an additional six hours with more reagents being added. The reaction mixture was then evaporated under reduced pressure and the residue was dissolved in 800 ml. of water. The solution was made acidic with hydrochloric acid and the resulting precipitate was filtered. The precipitate was dissolved in 1N sodium hydroxide and the solution was washed once with ethyl acetate. The basic solution was made acidic with hydrochloric acid and the precipitate was recovered by filtration. The precipitate was crystallized first from isopropyl alcohol/ethyl acetate/water and then recrystallized from isopropyl alcohol providing 10.3 g. of the desired title product, m.p. 203°–205° C., IR, NMR.
Analysis: $C_{19}H_{20}N_4O_3$;
Calc.: C, 64.76; H, 5.72; N, 15.90.
Found: C, 64.59; H, 5.92; N, 15.62.

EXAMPLES 33–44

Following the procedures of Example 32, the following compounds were prepared from the corresponding nitrile intermediate. In certain cases, tetramethylguanidinium azide was used in place of sodium azide and ammonium chloride.

33. 5-[4-(4-Acetyl-3-hydroxy-2-propylbenzyloxy)-benzyl]-tetrazole, m.p. 155°–157° C.
Analysis: $C_{20}H_{22}N_4O_3$;
Calc. C, 65.56; H, 6.05; N, 15.29.
Found C, 65.54; H, 6.00; N, 15.00.

34. 5-[4-(4-Acetyl-3-hydroxy-2-propylbenzyloxy)-2-hydroxyphenyl]-tetrazole, m.p. 198°–200° C.
Analysis: $C_{19}H_{20}N_4O_4$;
Calc.: C, 61.95; H, 5.47; N, 15.21.
Found: C, 61.71; H, 5.67; N, 15.19.

35. 5-[2-(4-[4-Acetyl-3-hydroxy-2-propylbenzyloxy]-phenyl)ethyl]-tetrazole, m.p. 138°–141° C.
Analysis: $C_{21}H_{24}N_4O_3$;
Calc.: C, 66.30; H, 6.36; N, 14.73.
Found: C, 66.13; H, 6.23; N, 14.71.

36. 5-[1-(4-[4-Acetyl-3-hydroxy-2-propylbenzyloxy]-phenyl)ethyl]-tetrazole, m.p. 70°–71° C.
Analysis: $C_{21}H_{24}N_4O_3$;
Calc.: C, 66.30; H, 6.36; N, 14.73.
Found: C, 66.54; H, 6.30; N, 14.88.

37. 5-[4-(4-Acetyl-3-hydroxy-2-propylbenzyloxy)-α,α-dimethylbenzyl]-tetrazole, m.p. 127°–129° C.
Analysis: $C_{22}H_{26}N_4O_3$;
Calc.: C, 66.99; H, 6.64; N, 14.20.
Found C, 63.64; H, 6.61; N, 14.05.

38. 5-[4-(4-Acetyl-3-hydroxy-2-propylbenzylthiomethyl)phenyl]-tetrazole, m.p. 148°–154° C.
Analysis: $C_{20}H_{22}N_4O_2S$;
Calc.: C, 62.80; H, 5.80; N, 14.65.
Found C, 62.77; H, 5.66; N, 14.76.

39. 5-[4-(4-Acetyl-3-hydroxy-2-methylbenzyloxy)-phenyl]-tetrazole, m.p. 188°–190° C.
Analysis: $C_{17}H_{16}N_4O_3$;
Calc.: C, 62.95; H, 4.97; N, 17.27.
Found: C, 62.69; N, 4.77; N, 17.09;

40. 5-[4-(4-Acetyl-3-hydroxy-2-propylbenzylthio)-phenyl]-tetrazole, m.p. 177°–179° C.
Analysis: $C_{19}H_{20}N_4O_2S$:
Calc.: C, 61.94; H, 5.47; N, 15.21.
Found: C, 61.91; H, 5.52; N, 15.16.

41. 5-[2-(6-[4-Acetyl-3-hydroxy-2-propylbenzyloxy]-naphthyl)]-tetrazole, m.p. 198°–200° C.
Analysis: $C_{23}H_{22}N_4O_3$;
Calc.: C, 68.64; H, 5.51; N, 13.92.
Found: C, 68.66; H, 5.61; N, 13.89.

42. 5-(4-[4-Acetyl-3-hydroxy-2-(2-methylpropyl)ben-zyloxy]benzyl)-tetrazole, m.p. 159°–161° C.
Analysis: $C_{21}H_{24}N_4O_3$;
Calc.: C, 66.30; H, 6.36; N, 14.73.
Found: C, 66.40; H, 6.52; N, 14.93.

43. 5-[4-(4-Acetyl-3-hydroxy-2-propylbenzylamino)-benzyl]-tetrazole, m.p. 156°–160° C.
Analysis: $C_{20}H_{23}N_5O_2$;
Calc.: C, 65.74; H, 6.34; N, 19.16.
Found: C, 65.52; H, 6.27; N, 18.89.

44. 5-[4-(4-Acetyl-3-hydroxy-2-ethylbenzyloxy)benzyl]-tetrazole, m.p. 162°–164° C.
Analysis: $C_{19}H_{20}N_4O_3$;
Calc.: C, 64.76; H, 5.72; N, 15.70.
Found: C, 64.52; H, 5.83; N, 15.67.

EXAMPLE 45

5-[4-(2-[4-Acetyl-3-hydroxy-2-propylphenyl]ethenyl)-phenyl]-tetrazole

To a solution of 13.1 g. of triphenylphosphine in 150 ml. of toluene were added 11.3 g. of 4-acetyl-3-hydroxy-2-propylbenzyl chloride. The solution was heated to reflux overnight and then cooled. The resulting precipitate was filtered affording 11.9 g. of the desired triphenylphosphonium chloride intermediate, m.p. 236°–238° C.
Analysis: $C_{30}H_{30}ClO_2P$;
Calc.: C, 73.69; H, 6.18.
Found C, 73.61; H, 6.25.

Two grams of the triphenylphosphonium salt were dissolved in 40 ml. of tetrahydrofuran and the solution was cooled to 5° C. by means of an external ice bath. To the solution were added 2 g. of the sodium salt of 1,1,1,3,3,3-hexamethyldisilazane. The solution was allowed to stir for 21 hours after which 0.53 g. of 4-cyanobenzaldehyde in 10 ml. of tetrahydrofuran were added. The reaction was allowed to stir overnight and was then poured into water. The aqueous solution was extracted with ethyl acetate and the organic layer was evaporated to dryness. The residue was redissolved in ethyl acetate, washed three times with water, dried over sodium sulfate and evaporated to dryness. The residue was purified by chromatography to provide 0.4 g. 4-[2-(4-acetyl-3-hydroxy-2-propylphenyl)ethenyl]-benzonitrile.

This nitrile intermediate was then transformed into 11.9 mg. of the desired title tetrazole product following the procedure of Example 32, m.p. 220°–222° C., NMR.

EXAMPLE 46

Ethyl 4-(4-acetyl-3-hydroxy-2-propylbenzylamino)benzoate

A solution of 6.8 g. of 4-acetyl-3-hydroxy-2-propylbenzyl chloride and 14.9 g. of ethyl 4-aminobenzoate in 200 ml. of acetonitrile was heated to reflux for 48 hours. An additional 9.9 g. of ethyl 4-aminobenzoate were added and the reaction was refluxed an additional 120 hours. The reaction mixture was cooled and concentrated in vacuo. The residue was dissolved in methylene chloride. The organic solution was washed first with a saturated sodium carbonate solution and then with water. The organic solution was then dried over sodium sulfate and evaporated to dryness. Chromatography of the residue afforded 7.4 g. of the desired title product. NMR.

EXAMPLE 47

4-(4-Acetyl-3-hydroxy-2-propylbenzylamino)benzoic acid

A solution of 7.1 g. of the ester prepared in Example 46 in 100 ml. of hydrochloric acid was heated to reflux for one hour. The precipitate which formed on cooling was recovered by filtration and dried to give 1.3 g. of the desired title product, m.p. 202°–204° C.
Analysis : $C_{19}H_{21}NO_4$;
Calc.: C, 69.70; H, 6.49; N, 4.28.
Found: C, 69.79; H, 6.57; N, 4.23.

EXAMPLE 48

4-(4-Acetyl-3-hydroxy-2-propylbenzyloxy)-1-butanol

To a suspension of 9.6 g. of a 50% oil dispersion of sodium hydride in 100 ml. of 1,4-butanediol were added 11.3 g. of 4-acetyl-3-hydroxy-2-propylbenzyl chloride. The reaction was stirred overnight at room temperature and then heated to 60° C. for six hours. The reaction mixture was then poured into water and extracted with ethyl acetate. The ethyl acetate solution was evaporated to dryness and the residue was purified by chromatography over silica gel to provide 4.1 g. of the desired title product. NMR.

EXAMPLE 49

5-[4-(4-Acetyl-3-hydroxy-2-propylbenzyloxy)butyl]-tetrazole

To a solution of 11.3 g. of 4-(4-acetyl-3-hydroxy-2-propylbenzyloxy)-1-butanol in 100 ml. of methylene chloride were added 8.3 g. of triethylamine. The solution was cooled to −30° C. and 4.1 g. of methanesulfonyl chloride were added in a dropwise manner. After the addition was complete, the solution was stirred cold for 30 minutes and then allowed to come to room temperature. The reaction mixture was washed twice with water, dried over sodium sulfate, and evaporated in vacuo to provide 13.6 g. of the methyl sulfonyl ester of the starting alcohol which was used without further purification.

A solution of 13.6 g. of the methyl sulfonyl ester and 7.5 g. of sodium cyanide in 150 ml. of dimethylsulfoxide was stirred overnight at room temperature. The reaction mixture was poured into water, extracted five times with ethyl acetate. The combined extracts were washed three times with water, dried over sodium sulfate and magnesium sulfate, and were filtered. The filtrate was evaporated in vacuo and the residue was purified by column chromatography to provide 6.0 g. of 4-(4-acetyl-3-hydroxy-2-propylbenzyloxy)pentanenitrile NMR.

The six grams of the nitrile intermediate were dissolved in 150 ml. of dimethylformamide. Under an argon atmosphere, 4.1 g. of sodium azide and 3.3 g. of ammonium chloride were added and the reaction mixture was heated to 125° C. for five hours. At this time an additional 4.1 g. of sodium azide and 3.3 g. of ammonium chloride were added and the heating was continued for an additional 20 hours. An additional 2.05 g. of sodium azide and 1.65 g. of ammonium chloride were then added and the reaction was heated an additional 22 hours. After the reaction solution cooled, 350 ml. of water were added. The solution was made basic with an aqueous sodium hydroxide solution and the solution was then extracted with a mixture of 70 ml. of ethyl acetate and 115 ml. of toluene. The layers were separated and the organic layer was washed four times with water. The combined basic water solution and water extracts were made acidic with hydrochloric acid. The desired product oiled out and was extracted with ethyl acetate. The ethyl acetate layer was dried over sodium sulfate, filtered and evaporated to dryness. The residue was purified by high pressure liquid chromatography to provide 2.56 g. of the desired title tetrazole, m.p. 79°-81° C.

Analysis: $C_{17}H_{24}N_4O_3$;
Calc.: C, 61.43; H, 7.28.
Found C, 61.29; H, 7.39.

EXAMPLE 50

2-(4-Acetyl-3-hydroxy-2-propylbenzyloxy)ethanol

Following the procedure of Example 48, 6.8 g. of 4-acetyl-3-hydroxy-2-propylbenzyl chloride and 150 ml. of ethylene glycol were reacted to provide 4.6 g. of the title alcohol. NMR.

Analysis: $C_{14}H_{20}O_4$;
Calc C, 66.65; H, 7.99.
Found: C, 66.45; H, 7.88.

EXAMPLE 51

4-[2-(4-Acetyl-3-hydroxy-2-propylbenzyloxy)ethoxy]-benzonitrile

Following the procedure of Example 49, 4.6 g. of the alcohol from Example 50 were first treated with methanesulfonyl chloride to provide the methyl sulfonyl ester which was then reacted with 12.0 g. of 4-cyanophenol to provide 4.9 g. of the title nitrile intermediate. NMR.

EXAMPLE 52

5-(4-[2-(4-Acetyl-3-hydroxy-2-propylbenzyloxy)ethoxy]phenyl)-tetrazole

The title product was prepared from the nitrile of Example 51 following the procedure of Example 32, m.p. 170°-172° C.

Analysis: $C_{21}H_{24}N_4O_4$;
Calc.: C, 63.62; H, 6.10; N, 14.13.
Found: C, 63.37; H, 6.21; N, 14.39.

EXAMPLE 53

5-[4-(4-Acetyl-3-hydroxy-2-propylbenzylsulfinylmethyl)phenyl]-tetrazole

A solution of 3.8 g. of 5-[4-(4-acetyl-3-hydroxy-2-propylbenzylthiomethyl)phenyl]-tetrazole in 1.5 ml. of 30% hydrogen peroxide, 100 ml. of acetic acid, and 50 ml. of methylene chloride was stirred for 24 hours at room temperature. The solution was evaporated in vacuo and the residue was dissolved in hot isopropyl alcohol. Water was added and the resulting precipitate was recovered by filtration. Recrystallization from isopropyl alcohol gave 0.8 g. of the title sulfoxide, m.p. 112°-116° C. NMR, IR.

Analysis: $C_{20}H_{22}N_4O_3S$;
Calc.: C, 60.28; H, 5.57; N, 14.06.
Found: C, 60.36; H, 5.50; N, 13.91.

The compounds of Formula I should be useful in treating any condition, including clinical conditions, which is characterized by excessive release of leukotrienes $C_4$, $D_4$, or $E_4$ These conditions include immediate type hypersensitivity reactions such as asthma. Evidence obtained over the past few years has shown the presence of leukotrienes in sputum of patients with chronic bronchitis (Turnbull, et al., *Lancet II*, 526 (1977)) and cystic fibrosis (Cromwell, et al., *Lancet II*, 164 (1981)), suggesting a role of leukotrienes in the pathology of those diseases. Furthermore, Lewis and colleagues [*Int. J. Immunopharmacology*, 4, 85 (1982)] have recently detected material in rheumatoid synovial fluid that reacts antigenically with antibody to $LTD_4$. This may hallmark the existence of leukotriene permeability factors that, together with $LTB_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes.

The term "excessive release" of leukotrienes refers to an amount of leukotrienes sufficient to cause the particular condition associated with such amount. The amount of leukotriene which is considered to be excessive will depend on a variety of factors, including the specific leukotriene(s) involved, the amount of leukotriene required to cause the particular condition, and the species of the mammal involved. As will be appreciated by those skilled in the art, the success of treating a mammal suffering from or susceptible to a condition characterized by an excessive release of leukotrienes with a compound of formula I will be measured by the regression or prevention of the symptoms of the condition.

Leukotriene antagonism was demonstrated by the following test procedure:

Male, Hartley guinea pigs weighing 200–450 grams were killed by decapitation. A section of terminal ileum was removed, the lumen cleaned, and the tissue divided into 2.5 cm. segments. The ilea were mounted in 10 ml. tissue baths containing Krebs-bicarbonate solution of the following composition in mmoles/liter; KCl, 4.6; $CaCl_2 \cdot 2H_2O$, 1.2; $KH_2PO_4$, 1.2; $MgSO_4 \cdot 7H_2O$, 1.2; NaCl, 118.2; $NaHCO_3$, 24.8; and dextrose, 10.0. The bath fluid was maintained at 37° C. and aerated with 95 percent oxygen and 5 percent $CO_2$. In addition, the buffer contained $1 \times 10^{-6}M$ atropine to reduce ileal spontaneous activity. Isometric measurements were made with a Grass FT03C force-displacement transducer and recorded on a Grass polygraph as change in grams of force. A passive force of 0.5 g. was applied to the tissues. After an appropriate equilibration period, single submaximal control responses to pure $LTD_4$ were obtained. Following a five minute exposure of the ileum to an experimental drug, the control concentration of $LTD_4$ was added to the tissue bath. The response of the ileum to $LTD_4$ in the presence of the drug was compared to the response in the absence of the drug.

For some of the drugs in this series a more detailed analysis of $LTD_4$ antagonism was made. In these experiments, cumulative concentration-response curves were obtained to $LTD_4$ in guinea pig ileum and trachea. This was followed by a 30 minute incubation with various concentrations of the experimental drug. The concentration response curve to $LTD_4$ was then repeated in the presence of the antagonist. Only one concentration of antagonist was used on a single tissue. $K_B$ values were calculated by the method of Furchgott [*Ann. N.Y. Acad. Sci.*, 139, 553 (1967)] using the following equation.

$$K_B = \frac{[\text{Antagonist}]}{\text{Dose Ratio} - 1}$$

Dose ratio refers to the concentration of agonist required to elicit 50 percent of the maximal response ($ED_{50}$) in the presence of the antagonist divided by the $ED_{50}$ in the absence of the antagonist. Calculations were performed with the aid of a computer and a digital plotter. The $pA_2$ is then calculated as the negative log of $K_B$ when the slope of the Schild plot is not significantly different from unity.

The testing of the compounds of Formula I in these two procedures is summarized in Table I.

TABLE I

| Compound of Example No. | Percent inhibition of $LTD_4$ evoked ileal contractions | | | | | | $pA_2$ |
|---|---|---|---|---|---|---|---|
| | $3 \times 10^{-6}M$ | $1 \times 10^{-6}M$ | $3 \times 10^{-7}M$ | $1 \times 10^{-7}M$ | $3 \times 10^{-8}M$ | $1 \times 10^{-8}M$ | |
| 10 | | 97 | 86 | 62 | | | 7.42 |
| 11 | 94 | 75 | | | | | 6.63 |
| 12 | | 91 | 77 | 66 | 37 | | 7.22 |
| 13 | | 97 | 85 | 69 | 59 | 30 | 7.57 |
| 14 | 67 | 31 | | | | | 5.75 |
| 15 | | 79 | 76 | 59 | | | 7.58 |
| 16 | | 88 | 88 | 54 | | | 7.06 |
| 17 | 35 | 5 | | | | | 5.35 |
| 18 | 65 | 21 | | | | | 5.68 |
| 32 | | 94 | 94 | 83 | | | 8.11 |
| 33 | | 100 | 94 | 92 | 81 | 31 | 8.12 |
| 34 | | | 98 | 97 | 80 | 50 | 8.06 |
| 35 | | | 90 | 84 | 63 | | 8.08 |
| 36 | | 94 | 90 | 89 | 70 | 44 | 7.90 |
| 37 | | | 90 | 81 | 56 | | 7.76 |
| 38 | | | 51 | 29 | | | 6.5 |
| 39 | | 90 | 70 | | | | 7.04 |
| 40 | | | | 79 | 58 | | 7.7 |
| 41 | | | | 90 | | 46 | 7.91 |
| 42 | | | 88 | 86 | 60 | 34 | 7.7 |
| 43 | | | | 77 | 49 | | 7.5 |
| 44 | | | | 88 | 78 | 41 | 7.9 |
| 45 | | 74 | 57 | | | | 6.73 |
| 47 | | 70 | 36 | | | | 6.31 |
| 49 | | 64 | 36 | | | | 6.26 |
| 52 | | | 83 | 67 | 39 | | 7.31 |
| 53 | 39 | | 4 | 14 | | | 5.2 |

The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to 500 mg. (from about 5 to 50 mg. in the case of parenteral or inhalation administration, and from about 25 to 500 mg. in the case of oral or rectal administration) of a compound of Formula I. Dosages of from about 0.5 to 300 mg./kg. per day, preferably 0.5 to 20 mg./kg., of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

I claim:

1. A compound of the formula

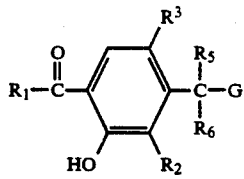

XVI wherein $R_1$ is hydrogen, $C_1$–$C_6$ alkyl, $C_3$–$C_8$ cycloalkyl, phenyl-substituted-($C_1$–$C_3$ alkyl), phenyl, or phenyl substituted with a halo, $C_1$–$C_4$ alkyl, or $C_1$–$C_4$ alkoxy group;

$R_2$ is $C_1$–$C_{10}$ alkyl, $C_2$–$C_6$ alkenyl, benzyl, or 2-phenylethyl;

$R_3$ is hydrogen, bromo, or chloro;

each of $R_5$ and $R_6$ is independently hydrogen, $C_1$–$C_3$ alkyl, phenyl, or benzyl; and G is chloro, bromo, iodo, hydroxy, thiol, —$NR_{18}R_{19}$, or —$P(C_6H_5)_3X'$, where each of $R_{18}$ and $R_{19}$ is independently hydrogen or $C_1$–$C_3$ alkyl and $X'$ is chloro, bromo, or iodo.

2. A compound of claim 1 wherein $R_1$ is methyl, $R_2$ is propyl, and $R_3$, $R_5$, and $R_6$ are each hydrogen.

3. The compound of claim 2 which is 4-acetyl-3-hydroxy-2-propylbenzyl chloride.

4. The compound of claim 2 which is 4-acetyl-3-hydroxy-2-propylbenzyl alcohol.

5. The compound of claim 2 which is 4-acetyl-3-hydroxy-2-propylbenzyl mercaptan.

6. The compound of claim 2 which is N,N-dimethyl-4-acetyl-3-hydroxy-2-propylbenzylamine.

* * * * *